United States Patent [19]
Yasushi et al.

[11] Patent Number: 5,241,967
[45] Date of Patent: Sep. 7, 1993

[54] SYSTEM FOR EVOKING ELECTROENCEPHALOGRAM SIGNALS

[75] Inventors: Mitsuo Yasushi; Yoshio Saito, both of Kawagoe, Japan

[73] Assignee: Pioneer Electronic Corporation, Tokyo, Japan

[21] Appl. No.: 712,999

[22] Filed: Jun. 10, 1991

Related U.S. Application Data

[63] Continuation of Ser. No. 372,594, Jun. 28, 1989, abandoned.

[30] Foreign Application Priority Data

Dec. 23, 1988 [JP] Japan ............... 63-323698
Dec. 23, 1988 [JP] Japan ............... 63-323699
Dec. 23, 1988 [JP] Japan ............... 63-323700

[51] Int. Cl.$^5$ ............... A61B 5/04
[52] U.S. Cl. ............... 128/732; 600/27
[58] Field of Search ............... 128/731, 732, 739, 745, 128/746, 905; 600/26-28

[56] References Cited

U.S. PATENT DOCUMENTS

| | | | |
|---|---|---|---|
| 3,837,331 | 9/1974 | Ross ............... | 128/732 |
| 3,893,450 | 7/1975 | Ertl ............... | 128/731 |
| 4,227,516 | 10/1980 | Meland et al. ............... | 600/26 |
| 4,228,807 | 10/1980 | Yagi et al. ............... | 128/732 |
| 4,462,411 | 7/1984 | Rickards ............... | 128/731 |

Primary Examiner—Lee S. Cohen
Assistant Examiner—J. P. Lacyk
Attorney, Agent, or Firm—Sughrue, Mion, Zinn, Macpeak & Seas

[57] ABSTRACT

A physiological change in the body of a user such as a brain wave or EEG signal is detected by electrodes attached to the scalp of the user. A frequency signal corresponding to a brain wave to be evoked is extracted by a bandpass filter from a signal which indicates the detected physiological change. The frequency signal is then applied to a stimulus generator which converts the frequency signal to a stimulative signal such as a photic stimulus and feeds the stimulative signal back to the user's body. The brain wave to be evoked is strongly synchronized by the stimulative signal applied to the user to place the user quickly into a desired brain wave state. The stimulative signal well matches the user's body since it originates from the signal representing the physiological change in the body of the user.

60 Claims, 9 Drawing Sheets

FIG. 7(a)
FIG. 8(a)
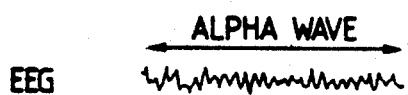
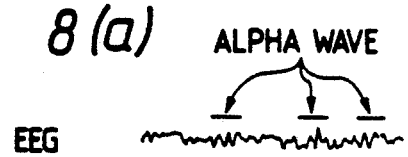
FIG. 7(b)
FIG. 8(b)
FIG. 9
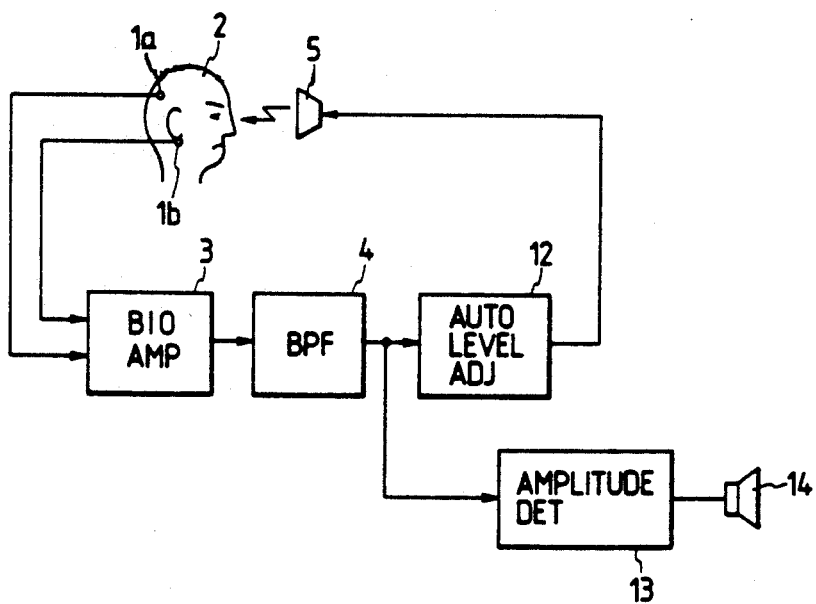

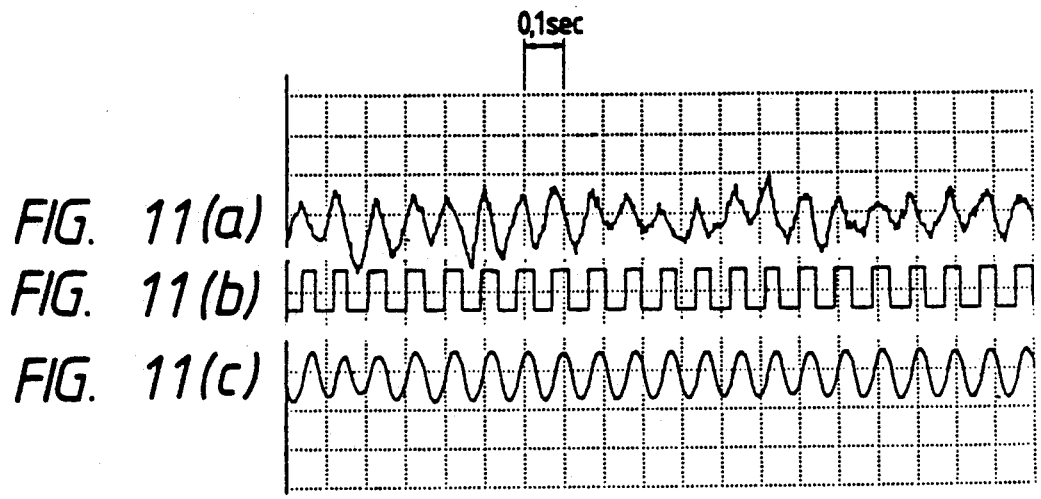
FIG. 11(a)
FIG. 11(b)
FIG. 11(c)
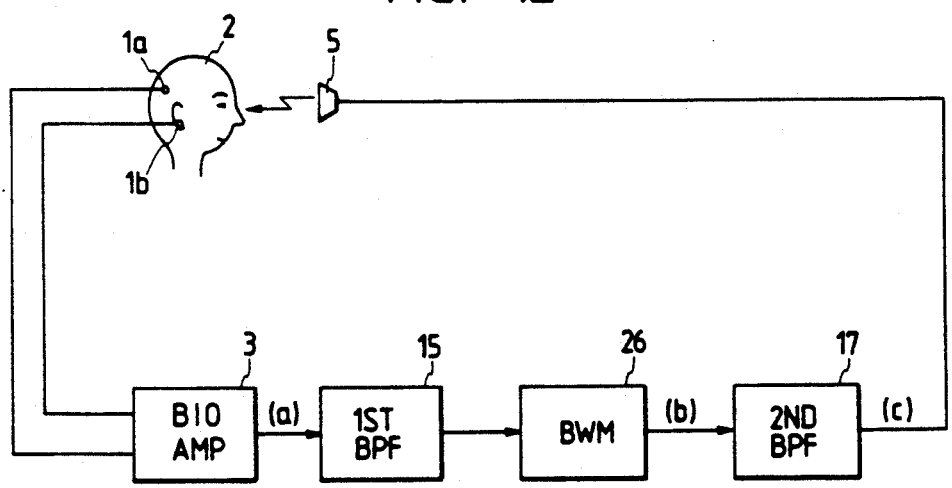
FIG. 12

FIG. 13
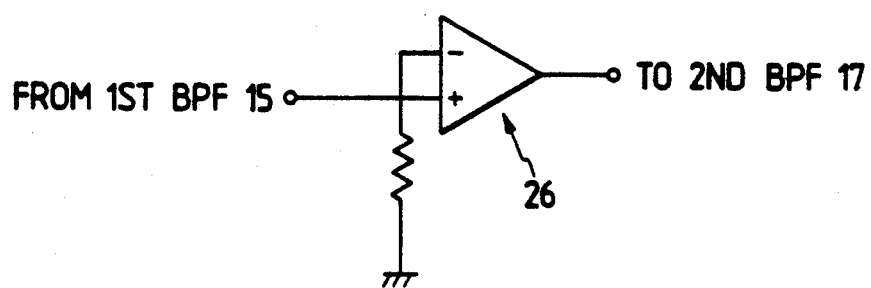
FIG. 14 (a)
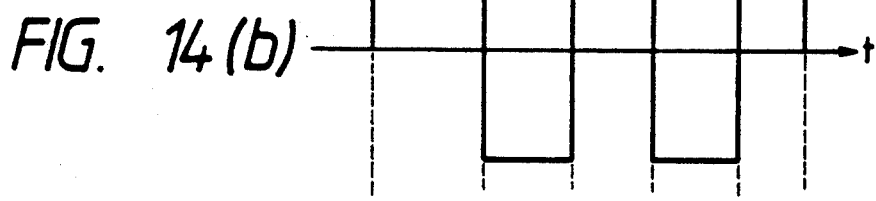
FIG. 14 (b)
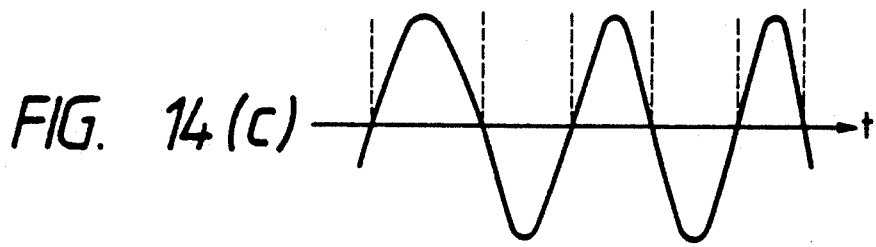
FIG. 14 (c)

SYSTEM FOR EVOKING ELECTROENCEPHALOGRAM SIGNALS

This is a continuation of application Ser. No. 07/372,594 filed Jun. 28, 1989, now abandoned.

BACKGROUND OF THE INVENTION

The present invention relates to a system for evoking a desired electroencephalogram signal, i.e., a brain wave, efficiently from a human brain.

It is known in the art that brain waves, i.e., electroencephalogram (EEG) signals, originating from the brain of a human being and the physiological and psychological states of the human being are closely related to each other. For example, when a human being is in a relaxed state, alpha ($\alpha$) waves in a frequency range of from about 8 to 13 Hz are dominantly produced. Beta ($\beta$) waves are prevalent in an active mental state and have a frequency ranging from about 14 to 30 Hz. Brain waves generated during drowsiness and light sleep are theta ($\theta$) waves in a frequency band ranging from about 4 to 7 Hz. The correlation between these brain waves having different frequency ranges and certain human activity phases indicates that the evocation of a certain brain wave through sensory stimulation is apt to put the human being in a corresponding physiological and psychological state.

Based on the analysis of the interaction between the EEG signals and physiological and psychological states, there have heretofore been proposed various systems for evoking alpha waves from the brain of a human being by giving a certain external stimulus to his body, to thereby place him in a physically and psychologically relaxed state for assisting him in lessening stresses and achieving mental concentration.

For example, Japanese Laid-Open Patent Publication No. 55-63656 discloses a biofeedback device for putting a user in a relaxed state by picking up brain waves through electrodes attached to the scalp of the user, extracting alpha waves from the brain waves, and varying sounds emitted from earphones worn by the user depending on the intensity of the alpha waves to let the user know how the alpha waves are being produced based on different sounds.

A relaxation device disclosed in Japanese Laid-Open Patent Publication No. 62-87165 includes a random noise generator for generating random noise to artificially produce an alpha wave signal having fluctuating 1/f characteristics. A light source is turned on and off by the alpha wave signal to apply a photic stimulus to a user for thereby placing the user in a relaxed state.

For the user to reach a relaxed state with the biofeedback device described above, it is necessary that the user differentiate differing sounds emitted from the earphones and control his psychological state according to his own will in order to make the sound corresponding to the alpha waves most intensive. Before the biofeedback device is used most effectively, therefore, the user has to repeatedly practice the device to find out how mental concentration should be effected to produce intensive alpha waves, so that the psychological state can freely be changed to some extent according to the user's own will. A person who uses the biofeedback device may not necessarily achieve the desired result, and hence the effectiveness of the device may vary from user to user.

The relaxation device disclosed in the latter publication employs an artificial alpha wave signal which has no direct relationship whatsoever to the brain waves of a user for evoking the brain waves. Accordingly, the evoked EEG responses are not constant and tend to differ from one user to another.

SUMMARY OF THE INVENTION

In view of the aforesaid drawbacks of the conventional electroencephalogram evoking systems, it is an object of the present invention to provide an electroencephalogram signal evoking system for quickly evoking a desired brain wave or electroencephalogram signal such as an alpha, beta, or theta wave, without the need for any preliminary training or practice on the part of a user of the system, by extracting only a signal corresponding to the desired brain wave from signals indicating physiological changes of the system user and feeding back the extracted signal as a stimulating signal to the system user. Another object of the present invention is to provide an electroencephalogram signal evoking system for quickly and intensively evoking a desired brain wave or electroencephalogram signal such as an alpha, beta, or theta wave, without the need for any preliminary training or practice on the part of a user of the system, by extracting only a signal having a frequency most suitable for evoking the desired brain wave from signals indicating physiological changes of the system user and feeding back the extracted signal as a stimulating signal to the system user.

Still another object of the present invention is to provide an electroencephalogram signal evoking system for efficiently evoking a desired brain wave or electroencephalogram signal such as an alpha, beta, or theta wave, without the need for any preliminary training or practice on the part of a user of the system, by extracting only a signal corresponding to the desired brain wave from signals indicating physiological changes of the system user, automatically adjusting the level of the extracted signal to a level suitable for evoking the brain wave, and feeding back the extracted signal as a stimulating signal to the system user.

Yet another object of the present invention is to provide an electroencephalogram signal evoking system for quickly and intensively evoking a desired brain wave or electroencephalogram signal, without the need for any preliminary training or practice on the part of a user of the system, by employing a stimulating signal in phase with the desired brain wave to stimulate the body of the user of the system.

Yet still another object of the present invention is to provide an electroencephalogram signal evoking system of a simple circuit arrangement for efficiently evoking a desired brain wave or electroencephalogram signal, without the need for any preliminary training or practice on the part of a user of the system.

It is also an object of the present invention to provide an electroencephalogram signal evoking system for efficiently evoking a desired brain wave or electroencephalogram signal, without the need for any preliminary training or practice on the part of a user of the system, by employing a detected signal indicating a physiological change of the system user and simultaneously letting the system user know aurally how the desired brain wave is evoked.

A still further object of the present invention is to provide an electroencephalogram signal evoking system for efficiently evoking a desired brain wave or electroencephalogram signal, without the need for any preliminary training or practice on the part of a user of the system, by detecting from the body of the system user signals indicative of physiological changes of the system user and relating to left and right cerebral hemispheres, stimulating the left cerebral hemisphere with the physiological change signal relating to the right cerebral hemisphere, stimulating the right cerebral hemisphere with the physiological change signal relating to the left cerebral hemisphere, and automatically adjusting the intensity of the stimulating signals to a level optimum for evoking the brain wave.

According to one aspect of the present invention, there is provided a system for evoking an electroencephalogram signal from the brain of a user of the system, comprising detecting means for detecting a physiological change in the body of the user and producing a signal indicative of the detected physiological change, filtering means for extracting a frequency signal corresponding to an electroencephalogram signal to be evoked from the signal produced by the detecting means, and stimulating means for converting the frequency signal extracted by the filtering means to a stimulative signal and applying the stimulative signal to the user.

According to another aspect of the present invention, there is also provided a system for evoking an electroencephalogram signal from the brain of a user of the system, comprising detecting means for detecting a physiological change in the body of the user and producing a signal indicative of the detected physiological change, a bandpass filter for extracting a frequency signal corresponding to an electroencephalogram signal to be evoked, from the signal produced by the detecting means, the bandpass filter having a variable passband, filter frequency control means for selecting a frequency optimum for evoking the electro-encephalogram signal by analyzing the frequencies of the signal produced by the detecting means, and for setting the central frequency of the passband of the bandpass filter to the selected frequency, and stimulating means :or converting the frequency signal extracted by the bandpass filter to a stimulative signal, and for applying the stimulative signal to the user.

According to still another aspect of the present invention, there is further provided a system for evoking an electroencephalogram signal from the brain of a user of the system, comprising detecting means for detecting a physiological change in the body of the user and producing a signal indicative of the detected physiological change, a bandpass filter for extracting a frequency signal corresponding to an electroencephalogram signal to be evoked, from the signal produced by the detecting means, level adjusting means for adjusting the amplitude level of the frequency signal from the bandpass filter to a predetermined level, and stimulating means for converting an output signal from the level adjusting means to a stimulative signal and for applying the stimulative signal to the user.

According to yet another aspect of the present invention, the system further comprises means for detecting the level of the evoked electroencephalogram signal from the amplitude of the frequency signal extracted by the bandpass filter and for aurally informing the person of the condition in which the electroencephalogram signal is evoked.

According to a further aspect of the present invention, there is provided a system for evoking an electroencephalogram signal from the brain of a user of the system, comprising detecting means for detecting a physiological change in the body of the user and producing a signal indicative of the detected physiological change, phase lock signal generator means for generating a signal having a constant level in phase with the signal produced by the detecting means, a bandpass filter for extracting a frequency signal corresponding to an electroencephalogram signal to be evoked from the signal produced by the phase lock signal generator means, and stimulating means for converting the frequency signal extracted by the bandpass filter to a stimulative signal and for applying the stimulative signal to the user.

According to a still further aspect of the present invention, there is provided a system for evoking an electroencephalogram signal from the brain of a user of the system, comprising detecting means for detecting a physiological change in the body of the user and producing a signal indicative of the detected physiological change, a first bandpass filter for extracting a frequency signal corresponding to an electroencephalogram signal to be evoked from the signal produced by the detecting means, pulse width modulator means for generating a signal of a constant level which has been pulse-width-modulated by the frequency signal from the first bandpass filter, a second bandpass filter for extracting a frequency signal corresponding to an electroencephalogram signal to be evoked, from the signal produced by the pulse width modulator means, and stimulating means for converting the frequency signal extracted by the second bandpass filter to a stimulative signal, and for applying the stimulative signal to the user.

According to a yet further aspect of the present invention, there is also provided a system for evoking electroencephalogram signals from right and left cerebral hemispheres, respectively, of the brain of a user of the system, comprising detecting means for detecting physiological changes in the body of the user relative to the right and left cerebral hemispheres from a plurality of areas on the body of the person, and for producing signals indicative of the detected physiological changes, a plurality of bandpass filters for extracting frequency signals corresponding to electroencephalogram signals to be evoked, from the signals produced by the detecting means, level adjusting means for adjusting the amplitude levels of the frequency signals from the bandpass filter to respective predetermined levels, and stimulating means for converting output signals from the level adjusting means to stimulative signals, respectively, and for feeding the stimulative signal based on the detected physiological change signal relative to the right cerebral hemisphere back to the left cerebral hemisphere and for feeding the stimulative signal based on the detected physiological change signal relative to the left cerebral hemisphere back to the right cerebral hemisphere.

The above and other objects, features and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIGS. 7(a) and (b) are diagrams showing a measured alpha wave evoked when a photic stimulus signal of an adequate level is applied;

FIGS. 8(a) and (b) are diagrams showing a measured alpha wave evoked when a photic stimulus signal that is too intensive is applied;

FIG. 9 is a block diagram of a system for evoking an electroencephalogram signal according to yet another embodiment of the present invention;

FIGS. 11(a)-(c) are diagrams illustrating the waveforms of signals produced in the EEG signal evoking system shown in FIG. 10;

FIG. 12 is a block diagram of a system for evoking an electroencephalogram signal in accordance with a still further embodiment of the present invention;

FIG. 13 is a block diagram of a pulse width modulator in the EEG signal evoking system shown in FIG. 12;

FIGS. 14(a)-(c) are diagrams showing the waveforms of signals produced in the EEG signal evoking system shown in FIG. 12;

DETAILED DESCRIPTION OF THE PREFERRED EMBODIMENTS

Figure 1:
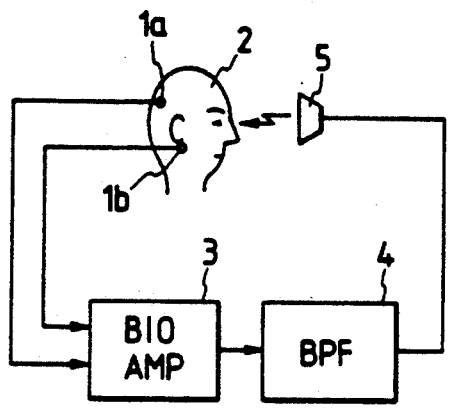
FIG. 1 is a block diagram of a system for evoking an electroencephalogram signal according to an embodiment of the present invention.

Like or corresponding parts are denoted by like or corresponding reference characters throughout the drawing views.

Brain waves or EEG signals of a human being tend to be synchronized by external stimulative signals applied to the body of the human being. The principles of the present invention are based on such synchronization of brain waves.

FIG. 1 shows in block form a system for evoking an electroencephalogram (EEG) signal or a brain wave in accordance with the present invention. The EEG signal evoking system shown in FIG. 1 employs an EEG signal as indicating a physiological change detected from the body of a system user, and also employs a photic stimulus as a stimulating signal to be applied to the user's body.

The EEG signal evoking system includes a pair of electrodes $1a$, $1b$ for picking up EEG signals or brain waves from the scalp 2 of the system user, a biological signal amplifier 3 for amplifying the EEG signals picked up by the electrodes $1a$, $1b$ to a signal level suitable for subsequent signal processing, a bandpass filter 4 coupled to the biological signal amplifier 3, and a photic stimulus generator 5 connected to the bandpass filter 4.

The bandpass filter 4 passes only a signal corresponding to a brain wave desired to be evoked. If an alpha wave having a frequency ranging from 8 to 13 Hz is to be evoked, then the central frequency of the passband of the bandpass filter 4 is selected to be $f_0 = 10$ Hz and sharpness Q of the bandpass filter 4 is selected to be $Q = 10$. If a theta wave having a frequency range of from 4 to 7 Hz is to be evoked, then the central frequency is selected to be $f_0 = 5$ Hz and the Q is selected to be $Q = 10$. If a beta wave having a frequency range of from 14 to 30 Hz is to be evoked, the central frequency is selected to be $f_0 = 20$ Hz and the Q is selected to be $Q = 4$.

The photic stimulus generator 5 generates stimulating light which flickers in synchronism with changes in the amplitude of a signal produced by the bandpass filter 4. The photic stimulus generator 5 may comprise a light-emitting device such as an LED and a driver for energizing the light-emitting device.

The electrodes $1a$, $1b$ and the photic signal generator 5 are incorporated in a headband (not shown), for example. When the headband is worn on the user's scalp 2, the electrodes $1a$, $1b$ contact the scalp 2 at prescribed positions thereon, and the light-emitting device of the photic stimulus generator 5 is positioned in front of an eye of the user. Therefore, brain waves can be picked up from the scalp 2 and a photic stimulus can be applied to the user quite easily at the same time.

Operation of the EEG signal evoking system for evoking an alpha wave, for example, will be described below. For alpha wave evocation, the central frequency of the pass band of the bandpass filter 4 is set $f_0 = 10$ Hz and the Q thereof is set to $Q = 10$, as described above.

The user wears the headband on the scalp 2 and the EEG signal evoking system is switched on. The electrodes $1a$, $1b$ pick up EEG signals or brain waves from the scalp 2 and send them to the biological signal amplifier 3 which amplifies the EEG signals. The amplified EEG signals are then fed to the bandpass filter 4 which selects and passes only a signal having a frequency around 10 Hz corresponding to that of the desired alpha wave. The signal from the bandpass filter 4 is then applied to the photic stimulus generator 5.

The photic stimulus generator 5 is responsive to the alpha wave signal sent from the bandpass filter 4 for turning on and off the light-emitting device such as an LED to radiate flickering light synchronous with the alpha wave as a photic stimulus toward the user.

When the flickering photic stimulus is applied or fed back to the user for visual stimulation, the alpha wave of the brain waves is synchronized by the flickering light an is strongly evoked. The evoked alpha wave is then picked up by the electrodes $1a$, $1b$ and sent to the biological signal amplifier 3, after which the above process is repeated.

Therefore, when the evocation of the alpha wave is started, a closed loop is established by the EEG signal evoking system and the user, thereby providing an oscillator which oscillates at &he frequency of the alpha wave signal that has been selected by the bandpass filter 4. Only a signal corresponding to the alpha wave to be evoked circulates through the closed loop, so that only the desired alpha wave is strongly evoked, rapidly bringing the user into a desired evoked EEG condition. As a result, the alpha wave of the brain waves becomes quickly intensive, and hence the percentage of the alpha wave in the brain waves and the peak value of the alpha wave are appreciably increased.

Figure 2A:
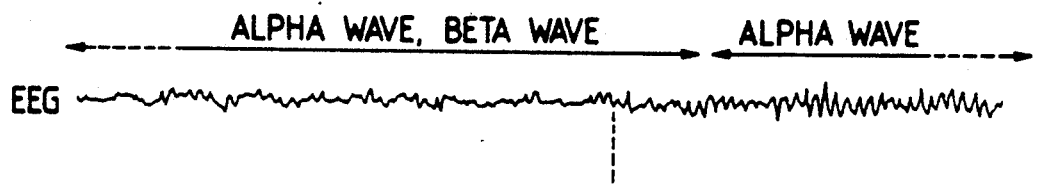
FIGS. 2(a) and (b) are diagrams showing a measured alpha wave evoked by the EEG signal evoking system shown in FIG. 1.
Figure 2B:
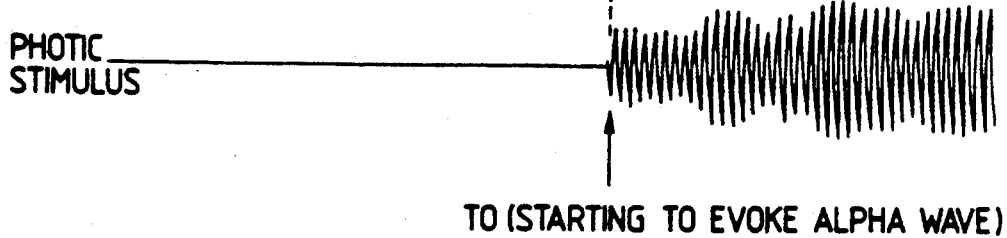

FIGS. 2(a) and (b) show the measured waveform of an alpha wave evoked by the EEG signal evoking system shown in FIG. 1. Brain waves picked up by the electrodes 1a, 1b are indicated in FIG. 2(a), whereas a photic stimulus signal applied to the user by the photic stimulus generator 5 is indicated in FIG. 2(b). The EEG signal evoking system is switched on at a time $t_0$ to start evoking the alpha wave.

It is apparent from FIGS. 2(a) and (b) that before the time $t_0$ when no alpha wave is evoked, brain waves including various waves such as alpha, beta, and other waves are present. When the EEG signal evoking system is turned on &o start to evoke the alpha wave, the alpha wave quickly becomes prevalent. Therefore, the EEG signal evoking system is highly effective in quickly putting the user in a relaxed state. Since a signal indicating a physiological change in the user's body is used as a stimulative signal applied to the user's body, the EEG signal evoking system of the invention well matches the user himself and is highly effective to evoke the desired brain wave.

In the above embodiment, although the biological signal amplifier 3 has been described as being a flat amplifier, the biological signal amplifier 3 may be imposed with a filtering characteristic. Specifically, in order to evoke theta wave having a frequency ranging from 0.5 to 7 Hz, the biological signal amplifier 3 may have a filtering characteristic such as to pass the EEG signal having a frequency ranging from 0.5 to 20 Hz. In this case, the bandpass filter 4 can be replaced with a low-pass filter allowing to pass the EEG signal having a frequency lower than 7 Hz. It would be apparent that a high-pass filter can also be employed in lieu of the bandpass filter 4 depending upon the filtering characteristic imposed to the biological signal amplifier.

Figure 3:
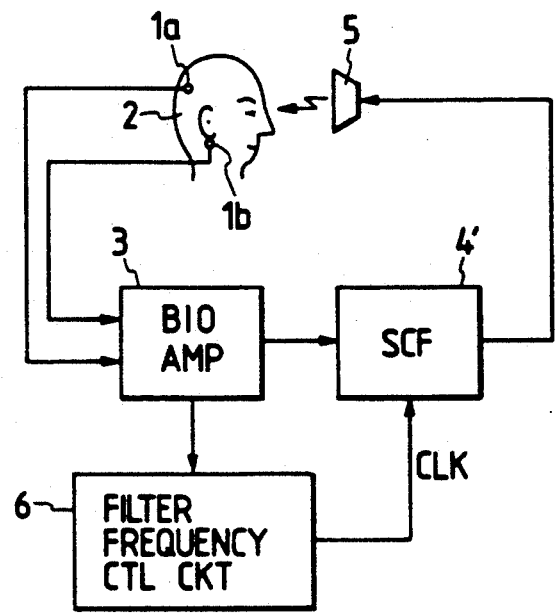
FIG. 3 is a block diagram of a system for evoking an electroencephalogram signal according to another embodiment of the present invention.
Figure 4:
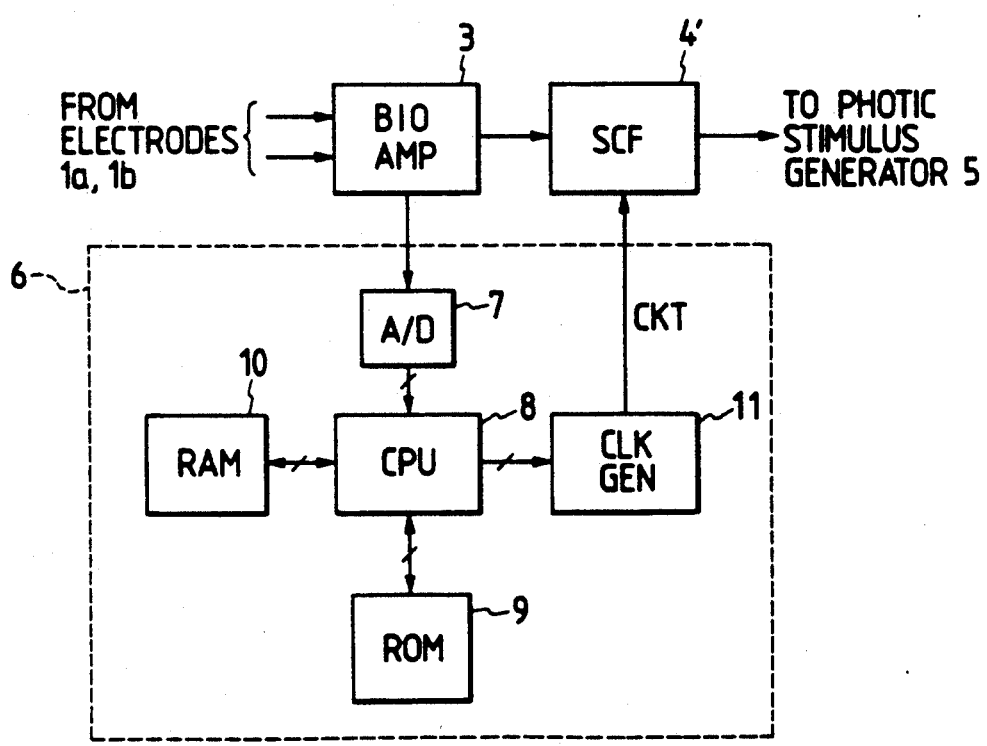
FIG. 4 is a block diagram of a filter frequency control circuit in the EEG signal evoking system illustrated in FIG. 3.

FIGS. 3 and 4 show an EEG signal evoking system according to another embodiment of the present invention. The EEG signal evoking system of FIGS. 3 and 4 differs from the EEG signal evoking system shown in FIG. in that a switched capacitor filter (SCF) 4' is used as a bandpass filter connected to the biological signal amplifier 3, and a filter frequency control circuit 6 is employed to vary the central frequency $f_0$ of the passband of the SCF 4'. Those components of the EEG signal evoking system which are identical to those shown in FIG. 1 will not be described in detail.

The SCF 4' is of a known construction and can freely vary the central frequency f of the passband thereof depending on the frequency of a clock signal applied thereto.

As shown in FIG. 4, the filter frequency control circuit 6 comprises an analog-to-digital (A/D) converter 7, a central processing unit (CPU) 8, a read-only memory (ROM) 9, a random-access memory (RAM) 10, and a clock generator 11. The filter frequency control circuit 6 analyzes the frequencies of the brain waves or EEG signals from the biological signal amplifier 3 through fast Fourier transform (FFT) or autocorrelation to produce a brain wave frequency spectrum, selects from the brain wave frequency spectrum a frequency that is most suitable for evoking a desired brain wave, and sets the central frequency $f_0$ of the passband of the SCF 4' to the selected frequency.

The frequencies of alpha wave produced by different users vary from one user to another and range from 8 to 13 Hz. If the photic stimulus signal has a fixed frequency of 10 Hz, for example, for evoking an alpha wave with its frequency ranging from 8 to 13 Hz, then alpha waves cannot equally effectively be evoked from different users. The EEG signal evoking system shown in FIGS. 3 and 4 is designed to solve this drawback.

In operation, the amplified brain waves or EEG signals are fed from the biological signal amplifier 3 to the SCF 4' and the filter frequency control circuit 6.

The brain waves delivered to the filter frequency control circuit 6 are converted by the A/D converter 7 to digital signals which are then applied to the CPU 8. The CPU 8 converts the time-base digital brain signal from the A/D converter 7 to a frequency-base brain wave spectrum by way of fast Fourier transform, and selects from the brain wave spectrum a frequency which is best suited to evoke a desired brain wave. The CPR 8 controls the frequency of the clock signal generated by the clock generator 11 in order to equalize the central frequency $f_0$ of the passband of the SCF 4' to the selected frequency. The clock generator 11 then supplies the clock signal with the controlled frequency to the SCF 4'. As a consequence, the central frequency $f_0$ of the passband of the SCF 4' is set to the optimum brain wave evoking frequency. The SCF 4' then only passes a signal present in the passband thereof having the central frequency $f_0$, and the signal from the SCF 4' is fed to the photic stimulus generator 5.

Accordingly, only the signal having the optimum frequency that has been selected by the filter frequency control circuit 5 circulates through the closed loop composed of the EEG signal evoking system and the user. An alpha wave, for example, is synchronized by the optimum frequency, and quickly and strongly evoked.

Figure 5A:
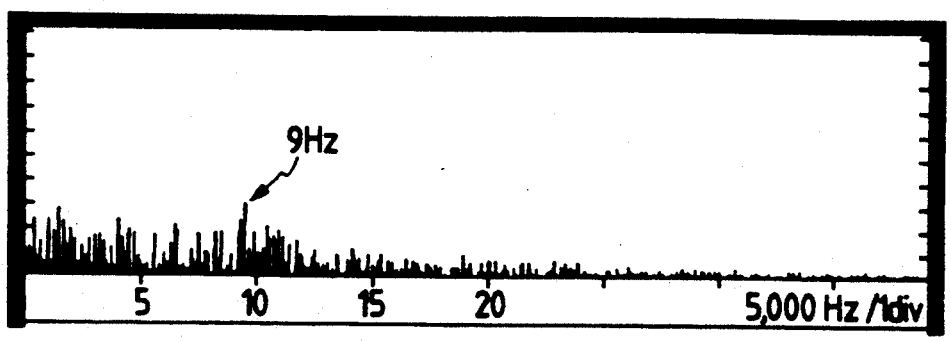
FIGS. 5(a) and 5(b) are diagrams showing the spectrums of alpha waves before and during photic stimulation in the EEG signal evoking system of FIG. 3.
Figure 5B:
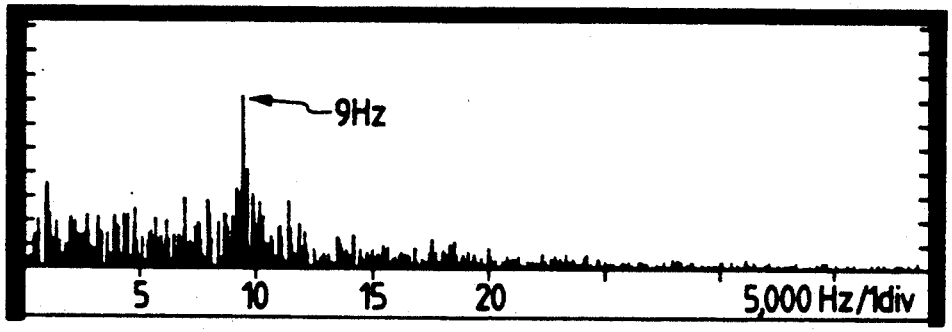

FIG. 5(a) shows a brain wave spectrum produced before a photic stimulus is applied to the user by the EEG signal evoking system of FIGS. 3 and 4, and FIG. 5(b) shows a brain wave spectrum produced while a photic stimulus is being applied to the user by the EEG signal evoking system shown in FIGS. 3 and 4.

A signal having a frequency of 9 Hz has a maximum spectral intensity in the alpha-wave frequency range of from 8 to 13 Hz in the brain wave spectrum produced before photic stimulation shown in FIG. 5(a). The frequency of 9 Hz is selected as the optimum brain wave evoking frequency by the filter frequency control circuit 6, which then automatically sets the central frequency $f_0$ of the SCF 4' to 9 Hz. Comparison between FIGS. 5(a) and 5(b) clearly indicates that the alpha wave having the frequency of 9 Hz is selectively evoked highly intensively by applying the photic stimulus to the user with the EEG signal evoking system shown in FIGS. 3 and 4.

Figure 6:
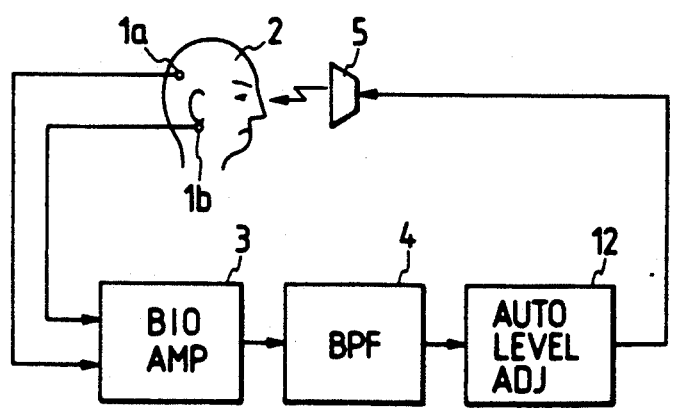
FIG. 6 is a block diagram of a system for evoking an electroencephalogram signal according to still another embodiment of the present invention.

FIG. 6 shows an EEG signal evoking system according to still another embodiment of the present invention. The EEG signal evoking system shown in FIG. 6 is similar to the EEG signal evoking system shown in FIG. 1 except that an automatic level adjusting circuit 12 is connected between the bandpass filter 4 and the photic stimulus generator 5. Those parts of the EEG signal evoking system which are identical to those shown in FIG. 1 will not be described in detail.

The automatic level adjusting circuit 12 comprises, for example, an automatic gain control (AGC) circuit for keeping a signal level at a constant level at all times, or a limiter or a clipper for holding the maximum amplitude of a signal below a certain level. An output signal from the automatic level adjusting circuit 12 is applied to the photic stimulus generator 5.

If a photic stimulus applied to the user were too weak, it would fail to synchronize a desired brain wave intensively enough, and if the photic stimulus applied to the user were too strong, its synchronizing effect would automatically be suppressed owing to the physiological and psychological protective reactions of the user's body. Unless the brain wave is evoked by a stimulative signal having an appropriate level, the amplitude of the evoked brain wave would periodically be increased and reduced, and the desired brain wave could not efficiently be evoked. The EEG signal evoking system shown in FIG. 6 is designed to avoid this shortcoming and evoke a desired brain wave efficiently.

The EEG signal evoking system shown in FIG. 6 operates as follows: The signal from the bandpass filter 4, which has a frequency near 10 Hz corresponding to that of a desired alpha wave, is applied to the automatic level adjusting circuit 12. The automatic level adjusting circuit 12 then adjusts the signal from the bandpass filter 4 to a predetermined level, and sends the alpha-wave signal with the adjusted level to the photic stimulus generator 5.

FIG. 7(a) and (b) show the measured waveform of an alpha wave which is evoked by the EEG signal evoking system when a photic stimulus signal is generated at an adequate level. FIGS. 8(a) and (b) illustrate the measured waveform of an alpha wave which is evoked when no level adjustment is effected on the signal from the bandpass filter 4 and a photic stimulus signal is too intensive.

If the photic stimulation applied to &he user is too strong as shown in FIG. 8(b), then the amplitude of an evoked alpha wave tends to vary periodically due to physiological and psychological protective reactions of the user. Therefore, the evoked alpha wave is intermittently produced as shown in FIG. 8(a). If the photic stimulation is of an adequate level as shown in FIG. 7(b), then the evoked alpha wave is continuously produced as shown in FIG. 7(a).

According to yet another embodiment shown in FIG. 9, an EEG signal evoking system includes, in addition to the system components shown in FIG. 6, an amplitude detector 13 connected to the output terminal of the bandpass filter 4 and an audible sound generator 14 such as a loudspeaker, an earphone, an electronic buzzer, or the like.

Brain waves or EEG signals are usually evoked from the brain of the user while the eyes of the user are being fully or partly closed. Therefore, for efficient brain wave evocation, it is preferable to let the user know aurally the level of the evoked brain wave to allow the user to confirm the condition in which the brain wave is evoked while the brain wave is being evoked. The EEG signal evoking system illustrated in FIG. 9 permits the user to confirm aurally the level of the evoked brain wave.

The amplitude detector 7 monitors the amplitude level of a brain wave signal produced by the bandpass filter 4 and detects the level of the brain wave evoked a& the time depending on the magnitude of the detected amplitude level. The amplitude detector 13 then applies an audio signal commensurate with the level of the evoked brain wave to the audible sound generator 14.

When an alpha wave starts being evoked by the EEG signal evoking system, the amplitude detector 13 monitors the alpha wave signal generated by the bandpass filter 4 and detects the level of the evoked alpha wave at the time based the magnitude detector 13 generates an audio signal depending on the magnitude of the level of the evoked alpha wave, and applies the audio signal to the audible sound generator 14. The audible sound generator 14 then generates a sound to let the user know aurally how the desired alpha wave is evoked. The user can thus confirm the condition in which the alpha wave is evoked while the alpha wave is being evoked.

Figure 10:
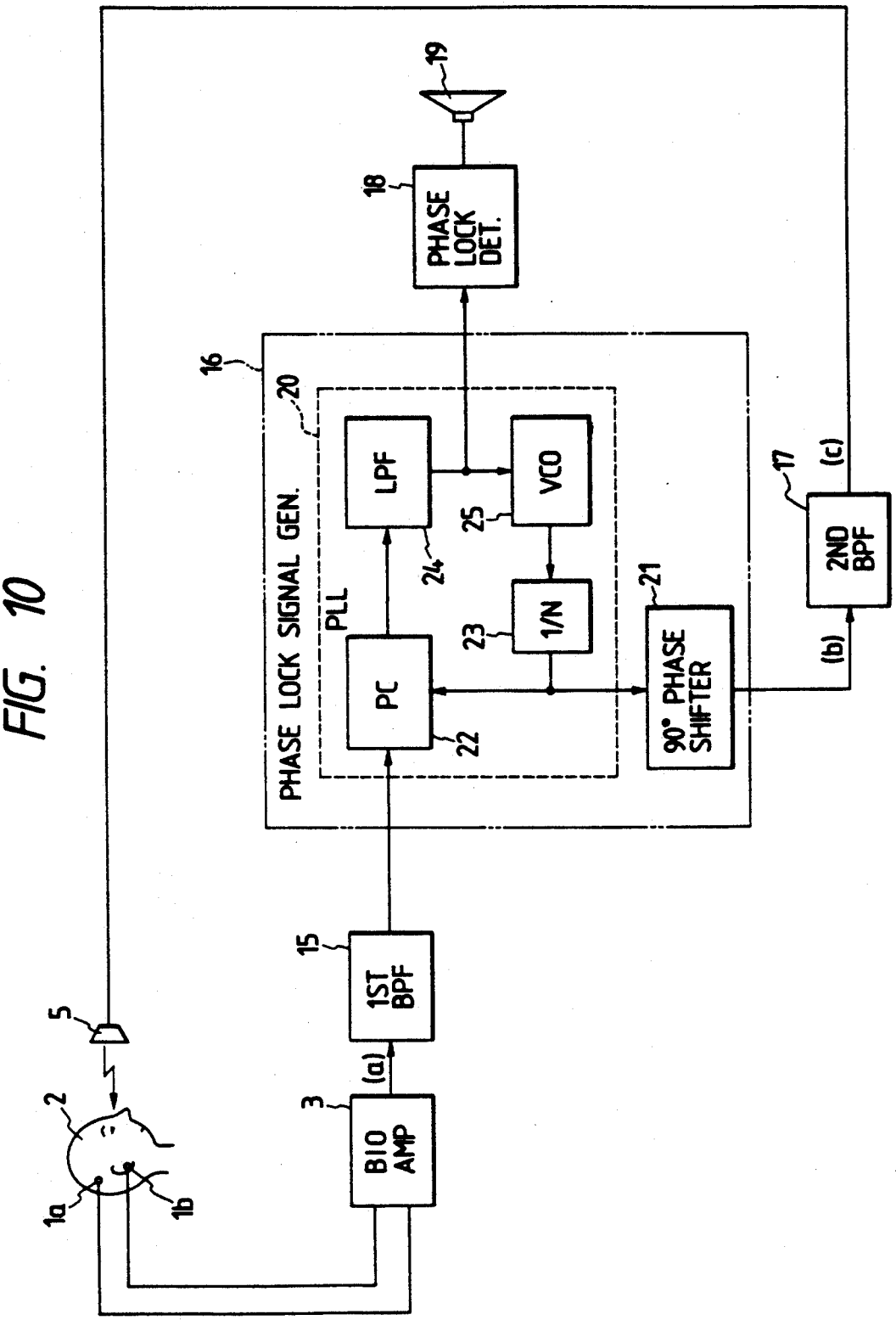
FIG. 10 is a block diagram of a system for evoking an electroencephalogram signal in accordance with a further embodiment of the present invention.

FIG. 10 shows in block form a system for evoking an electroencephalogram signal according to a further embodiment of the present invention. The EEG signal evoking system shown in FIG. 10 has the electrodes 1a, 1b, the biological signal amplifier 3, and the photic stimulus generator 5 which are identical to those of the EEG signal evoking system shown in FIG. 1. The EEG signal evoking system of FIG. 10 additionally includes a first bandpass filter 15 for removing noise from brain wave signals sent from the biological signal amplifier 3, a phase lock signal generator 16 for generating a rectangular wave signal of a constant level in phase with the brain wave signal from the first bandpass filter 15, a second bandpass filter 17 for extracting only a certain frequency signal corresponding to a brain wave to be evoked, from the rectangular wave signal produced by the phase lock signal generator 16 and passing only the extracted frequency signal, a phase lock detector 18 for monitoring the phase locked condition of the phase lock signal generator 16 to detect brain wave fluctuations, and an audible sound generator 19 such as a loudspeaker, an earphone, an electronic buzzer, or the like for informing the user of the detected brain wave fluctuations as an audible sound. The output signal from the second bandpass filter 17 is applied to the photic stimulus generator 5 which generates and gives a corresponding photic stimulus to the user.

The phase lock signal generator 16 serves to keep an evoked brain wave in phase with a stimulative signal applied or fed back to the user. Synchronization of the evoked brain wave by the stimulative signal becomes intensive and the brain wave is highly effective evoked when the evoked brain wave is kept in phase with the stimulative signal. The EEG signal evoking system shown in FIG. 10 is designed to effect such high brain wave evocation.

Each of the first and second bandpass filters 15, 17 serves to selectively pass a frequency signal corresponding to a brain wave to be evoked The passband of each of the first and second bandpass filters 15, 17 is selected to range from 8 to 13 Hz if an alpha wave is to be evoked, from 4 to 7 Hz if a beta wave is to be evoked, and from 14 to 30 Hz if a theta wave is to be evoked. Since the first bandpass filter 15 primarily serves to remove noise from the brain waves, the passband of the first bandpass filter 15 may be wider than that of the second bandpass filter 17, or the first bandpass filter 15 may be dispensed with in some applications.

The phase lock signal generator 16 comprises a phase-locked loop (PLL) 20 for generating a square wave signal having the same frequency as that of an input signal applied from the first bandpass filter 15 to the PLL 20, and a 90° phase shifter 21 for shifting the phase of the square wave signal generated by the PLL 20. The PLL 20 comprises a phase comparator (PC) 22, a 1/N frequency divider 23, a low-pass filter (LPF) 24, and a voltage-controlled oscillator (VCO) 25.

In operation, noise except an alpha wave signal is removed by the first bandpass filter 15 from the brain waves or EEG signals amplified by the biological signal amplifier 3, and the alpha wave signal is then supplied to the phase lock signal generator 16.

The alpha wave signal from the first bandpass filter 15 is applied to the PC 22 in which it is compared with a frequency-divided signal from the 1/N frequency divider 23. The PC 22 then issues a voltage proportional to the phase difference between the alpha wave signal and the frequency-divided signal. The voltage is then converted by the LPF 24 to a DC voltage which is applied to the voltage-controlled oscillator 25.

In response to the applied DC voltage, the voltage-controlled oscillator 25 generates a square wave signal having a frequency which is N times the frequency of the alpha wave signal applied to the phase comparator 22. The square wave signal is then applied from the voltage-controlled oscillator 25 to the 1/N frequency divider 23 which frequency-divides the square wave signal by N. Therefore, the 1/N frequency divider 23 issues a square wave signal having the same frequency as that of the alpha wave.

Because of the operational characteristics of the PLL 20, the wave signal issued by the 1/N frequency divider 13 leads the input signal applied to the phase comparator 12, i.e., the alpha wave signal, by 90°. Thus, the square wave signal from the 1/N frequency divider 23 is applied to the 90° phase shifter 21, so that the phase of the square wave signal is delayed 90° thereby. The square wave signal produced from the 90° phase shifter 21 has a constant level and is in phase with the alpha wave signal.

The second bandpass filter 17 extracts, from the square wave signal from the 90° phase shifter 21, a frequency signal having a frequency ranging from 8 to 13 Hz and hence corresponding to an alpha wave to be evoked, and passes the extracted frequency signal to the photic stimulus generator 5.

Since the alpha wave signal circulating through the loop composed of the EEG signal evoking system and the user is locked in phase with the alpha wave produced by the user and picked up by the electrodes 1a, 1b, the stimulating light which is fed back to the user by the photic stimulus generator 5 flickers in phase with the alpha wave of the user. Consequently, the desired alpha wave is intensively and quickly evoked because it is strongly synchronized by the photic stimulus signal.

The phase lock detector 18 monitors the DC voltage produced by the LPS 14 for variations. Any fluctuations in the frequency of the brain wave picked up by the electrodes 1a, 1b are detected based on the variations in the DC voltage. Such detected brain wave fluctuations are aurally notified to the user through the audible sound generator 19. Consequently, the desired brain wave can be evoked while the use is aurally confirming the condition in which it is evoked.

FIGS. 11(a)-(c) illustrate the waveforms of signals produced at corresponding points (a), (b), (c) in the EEG signal evoking system. Study of FIGS. 11(a)-(c) clearly shows that the alpha wave picked up by the electrodes 1a, 1b, the square wave signal produced by the phase lock signal generator 20, and the output signal from the second bandpass filter 17 are in phase with each other. It will therefore be understood that the alpha wave is strongly synchronized by the photic stimulus signal produced by the photic stimulus generator 5.

The photic signal and the evoked alpha wave signal may be brought into phase with each other by a suitable phase correcting or shifting arrangement in the bandpass filter 4, the automatic level adjusting circuit 12, or the photic stimulus generator 5 in FIG. 9, rather than by the phase lock signal generator 16 shown in FIG. 10.

FIG. 12 shows system for evoking an electroencephalogram signal according to a still further embodiment of the present invention. The EEG signal evoking system shown in FIG. 12 differs from the EEG signal evoking system illustrated in FIG. 10 only in that a pulse width modulator 26 is employed in place of the phase lock signal generator 16 in FIG. 10. Those parts which are identical to those shown in FIG. 10 will not be described in detail.

The pulse width modulator 26 serves to generate a square wave signal having a constant level which has been pulse-width-modulated by the brain wave signal applied from the first bandpass filter 15. The pulse width modulator 26 may comprise a known comparator, for example, as shown in FIG. 13.

The EEG signal evoking system shown in FIG. 12 operates in the following manner: A brain wave signal picked up by the electrodes 1a, 1b is amplified by the biological signal amplifier 3 into a signal (shown in FIG. 14(a), and then a frequency signal corresponding to an alpha wave is selected from the amplified signal by the first bandpass filter 15 and applied to the pulse width modulator 26.

The pulse width modulator 26 generates a square wave signal which has been pulse-width-modulated by the alpha wave signal from the first bandpass filter 15, the square wave signal having a constant level and a pulse width $W_p$ that varies depending on the alpha wave signal, as shown in FIG. 14(b). The square wave signal generated by the pulse width modulator 26 is therefore substantially in phase with the alpha wave signal applied to the pulse width modulator 26.

The second bandpass filter 17 extracts, from the square wave signal from the pulse width modulator 26, a frequency signal having a frequency ranging from 8 to 13 Hz and hence corresponding to an alpha wave to be evoked, and passes the extracted frequency signal to the photic stimulus generator 5.

As with the EEG signal evoking system shown in FIG. 10, the alpha wave picked up by the electrodes 1a, 1b, the square wave signal produced by the pulse width modulator 26, and the output signal from the second bandpass filter 17 are in phase with each other, as shown in FIGS. 11(a)-(c). Therefore, the alpha wave is strongly synchronized by the photic stimulus signal produced by the photic stimulus generator 5.

Figure 15:
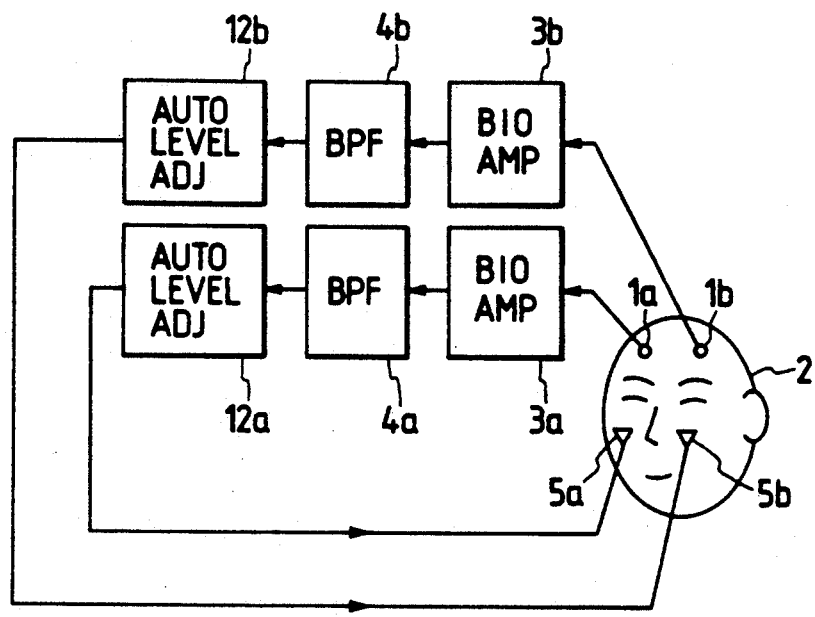
FIG. 15 is a block diagram of a system for evoking an electroencephalogram signal according to a yet further embodiment of the present invention.

FIG. 15 shows a system for evoking an electroencephalogram signal according to a yet further embodiment of the present invention.

Cerebrum physiology shows that the right and left cerebral hemispheres of the brain of a human being perform different functions. The left cerebral hemisphere chiefly governs the physiological and physical activities of the righthand half of the body, whereas the right cerebral hemisphere mainly controls the physiological and physical activities of the lefthand half of the body. Even when one of the cerebral hemispheres is placed in a brain wave evoking condition, the other cerebral hemisphere may not necessarily be put in the same brain wave evoking condition.

Generally, brain waves can most effectively be evoked from the right and left cerebral hemispheres when the brain waves are evoked synchronously. Desired brain waves can thus be evoked more effectively not only by employing a signal indicating a physiological change in the body of the user as a stimulative signal, but also by stimulating the right cerebral hemisphere with a stimulative signal originating from the left cerebral hemisphere and stimulating the left cerebral hemisphere with a stimulative signal originating from the right cerebral hemisphere so that the right and left cerebral hemispheres will be stimulated by each other's brain waves. The EEG signal evoking system shown in FIG. 15 is arranged to evoke brain waves by feeding stimulative signals back to the right and left cerebral hemispheres.

The EEG signal evoking system shown in FIG. 15 includes a pair of electrodes 1a, 1b attached respectively to right and left portions of the forehead of the scalp 2 of a user to pick up brain waves or EEG signals, a pair of biological signal amplifiers 3a, 3b for amplifying the EEG signals to signal levels suitable for subsequent signal processing, a pair of bandpass filters 4a, 4b connected to the respective biological signal amplifiers 3a, 3b, a pair of automatic level adjusting circuits 12a, 12b connected respectively to the bandpass filters 4a, 4b, and a pair of photic stimulus generators 5a, 5b.

Each of the biological signal amplifiers 3a, 3b is identical to the biological signal amplifier 3 shown in FIG. 1. Each of the bandpass filters 4a, 4b is identical to the bandpass filter 4 shown in FIG. 1. Each of the automatic level adjusting circuits 12a, 12b is identical to the automatic level adjusting circuit 12 shown in FIG. 6. Each of the photic stimulus generators 5a, 5b is identical to the photic stimulus generator 6 illustrated in FIG. 1. Therefore, the biological signal amplifiers 3a, 3b, the bandpass filters 4a, 4b, the automatic level adjusting circuits 12a, 12b, and the photic stimulus generators 5a, 5b will now be described in detail below.

The electrodes 1a, 1b and the photic stimulus generators 5a, 5b are mounted on a headband, for example, such that when the user wear the headband on the scalp 2, the electrodes 1a, 1b will be held respectively against the right and left portions of the forehead and the photic stimulus generators 5a, 5b will be positioned in front of the right and left eyes, respectively, of the user.

Operation of the EEG signal evoking system for evoking an alpha wave, for example, will be described below. For alpha wave evocation, the central frequency of the pass band of each of the bandpass filters 4a, 4b is set $f_0 = 10$ Hz and the Q thereof is set to $Q = 10$.

The user wears the headband on the scalp 2 and the EEG signal evoking system is switched on. The electrodes 1a, 1b pick up EEG signals or brain waves originating from the right and left cerebral hemispheres of the brain, and send them to the respective biological signal amplifiers 3a, 3b which amplify the EEG signals. The amplified EEG signals are then fed to the bandpass filters 4a, 4b which each select and pass only a signal having a frequency around 10 Hz corresponding to that of the desired alpha wave. The signals from the bandpass filters 4a, 4b are then applied to the automatic level adjusting circuits 12a, 12b, respectively, which adjust the signals to a predetermined level. The level-adjusted signals are then delivered to the photic stimulus generators 5a, 5b.

The photic stimulus generators 5a, 5b are responsive to the alpha wave signals sent from the automatic level adjusting circuits 12a, 12b for turning on and off the light-emitting devices such as LEDs with the alpha wave signals originating from the right and left cerebral hemispheres. The light-emitting devices radiate flickering light synchronous with these alpha wave signals as photic stimuli to the right and left eyes, respectively, of the user in order to evoke desired alpha waves.

The alpha waves evoked from the right and left cerebral hemispheres are picked up again by the respective electrodes 1a, 1b and sent to the biological signal amplifiers 3a, 3b, after which the above process is repeated.

Figure 16:
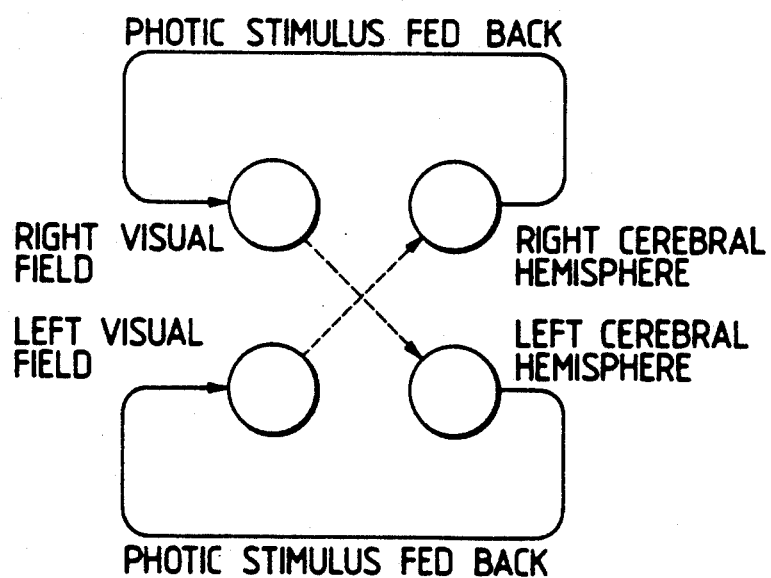
FIG. 16 is a diagram showing the principles of operation of the EEG signal evoking system shown in FIG. 15.

As shown in FIG. 16, the right and left cerebral hemispheres of a brain are linked to left and right visual fields by a nervous system. More specifically, the optic nerve for carrying sensation of sight from the right visual field of a right eye is connected to the left cerebral hemisphere, and the optic nerve for carrying sensation of sight from the left visual field of a left eye is connected to the right cerebral hemisphere. Therefore, a photic stimulus applied to the right eye stimulates the left cerebral hemisphere, and a photic stimulus applied to the left eye stimulates the right cerebral hemisphere. When the photic stimuli in the form of flickering light are applied by the photic stimulus generators 5a, 5b to the right and left eyes of the user, the photic stimulus produced by the alpha wave originating from the right cerebral hemisphere is applied through the right visual field to the left cerebral hemisphere to evoke an alpha wave therefrom, and the photic stimulus produced by the alpha wave originating from the left cerebral hemisphere is applied through the left visual field to the right cerebral hemisphere to evoke an alpha wave therefrom.

Consequently, when the evocation of the alpha waves is started, a closed loop is established by the EEG signal evoking system and the user, thereby providing an oscillator including the left and right cerebral hemispheres in series with each other, as shown in FIG. 2. Only signals indicating alpha waves that are to be evoked circulates through the closed loop which extends from the right cerebral hemisphere to the right visual field to the left cerebral hemisphere to the left visual field. As a result, desired alpha waves are intensively and quickly evoked from the right and left cerebral hemispheres of the brain of the user by being synchronized by the signals circulating through the closed loop.

Figure 17:
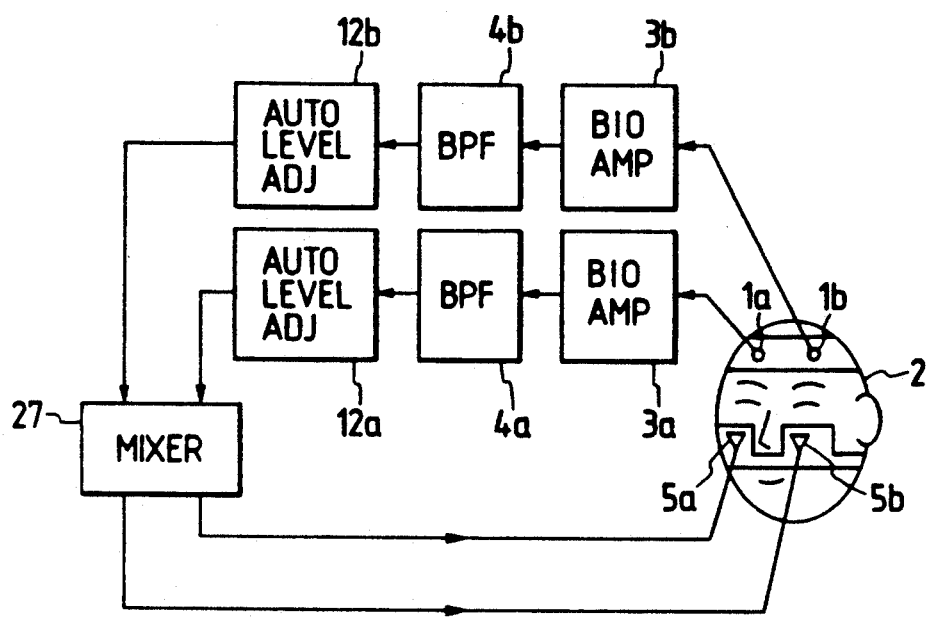
FIG. 17 is a block diagram similar to FIG. 15, showing an EEG signal evoking system according to another embodiment of the present invention.

FIG. 17 illustrates an EEG signals evoking system according to another embodiment of the present invention. The EEG signal evoking system of FIG. 17 is similar to the EEG signal evoking system of FIG. 15 except that a mixer 27 is connected to the output terminals of the automatic level adjusting circuits 12a, 12b for mixing detected alpha wave signals from the right and left cerebral hemispheres and sending the mixed signals to the photic stimulus generators 5a, 5b.

According to the EEG signal evoking system shown in FIG. 17, the right and left cerebral hemispheres of the user's brain are stimulated not only by each other's brain waves but also by brain waves of their own. Thus, even if either one of the right and left cerebral hemispheres in the closed loop has a lower level of evoked response, or even if the gain of the closed loop is low at the start of brain wave evocation, stable brain waves can be evoked.

While the alpha waves are evoked in the illustrated embodiments, theta and beta waves can also be evoked in the same manner as described above by varying the passbands of the bandpass filters used. It should be noted that in order to evoke the alpha waves, the EEG signals having frequencies ranging from 7 to 20 Hz, preferably 8 to 13 Hz need to be extracted. In order to evoke the beta waves, the EEG signals having frequencies ranging from 14 to 30 Hz need to be extracted. In order to evoke the theta waves, the EEG signals having frequencies ranging from 0.5 to 7 Hz, preferably 4 to 7 Hz need to be extracted. As a signal indicative of a physiological change of the user, there may be used a magnetoencephalogram signal, an electrodermogram signal, a dermal vibration, a dermal resistance, or the like, which has a certain correlation to an EEG signal. If an electro-dermogram signal, a dermal vibration, or a dermal resistance is employed, the electrodes 1a, 1b or any of other suitable means for detecting a physiological change signal are attached to suitable body parts such as wrists. Any of an aural stimulus, an electric stimulus, and a vibratory stimulus may be used instead of a photic stimulus to stimulate the body of the system user. If an aural stimulus is used, then suitable means for applying such aural stimulus is positioned near an ear of the user. If an electric or vibratory stimulus is to be fed back to the user's body, then a suitable means for applying such an electric or vibratory stimulus is attached to a suitable body part such as a wrist.

Although certain preferred embodiments have been shown and described, it should be understood that many changes and modifications may be made therein without departing from the scope of the appended claims.

What is claimed is:

1. A system for passively evoking a desired electroencephalogram signal from a brain of a user of the system, comprising:
    detecting means for detecting a physiological change in the user's body and producing a signal indicative of the detected physiological change;
    filtering means for extracting a desired electroencephalogram signal from the signal detected by said detecting means; and
    stimulating means for applying, as a stimulative signal, one of a photic, aural and vibratory signal to the user, the frequency of the applied stimulative signal being in synchronism with the frequency of said extracted electroencephalogram signal in order passively to evoke the desired electroencephalogram signal from the user.

2. A system according to claim 1, further comprising an amplifier connected to said detecting means for amplifying the signal indicative of the detected physiological change and producing in an output thereof an amplified signal, and wherein said filtering means comprises a bandpass filter and is connected to the output of said amplifier for extracting the frequency signal corresponding to the electroencephalogram signal produced by said amplifier, the frequency signal being converted to the stimulative signal having a variant amplitude.

3. A system according to claim 2, wherein the frequency signal represents a theta wave having a frequency ranging from 0.5 to 7 Hz.

4. A system according to claim 2, wherein the frequency signal represents an alpha wave having a frequency ranging from 7 to 20 Hz.

5. A system according to claim 2, wherein said detecting means comprises a pair of electrodes attachable to a scalp of the user.

6. A system according to claim 2, wherein said stimulating means comprises a light emitting diode and a driver for energizing said light emitting diode.

7. A system according to claim 6, wherein said stimulating means provides a photic stimulus to the user in synchronism with changes in the amplitude of the stimulative signal.

8. A system according to claim 2, wherein said stimulating means applies an aural stimulus to the user.

9. A system according to claim 2, wherein said stimulating means applies a vibratory stimulus to the user.

10. A system according to claim 5, wherein said detecting means and said stimulating means are incorporated in a headband attachable to the user.

11. A system according to claim 1 wherein said filtering means comprises:
    a bandpass filter for extracting a frequency signal corresponding to the electroencephalogram signal to be evoked from the signal produced by said detecting means, said bandpass filter having a variable passband, the passband having a central frequency; and
    filter frequency control means for selecting a frequency optimum for evoking the electroencephalogram signal by analyzing the signal produced by said detecting means and setting the central frequency of the passband of said bandpass filter to the selected frequency.

12. A system according to claim 1, further comprising an amplifier connected to said detecting means for amplifying the signal indicative of the detected physiological change and producing in an output thereof an amplified signal, wherein said bandpass filter is connected to the output of said amplifier for extracting the frequency signal corresponding to the electroencephalogram signal produced by said amplifier, the frequency signal being converted to the stimulative signal having a variant amplitude, and wherein said filter frequency control means is further connected to the output of said amplifier for selecting the frequency optimum for evoking the electroencephalogram signal by analyzing the amplified signal.

13. A system according to claim 12, wherein the frequency signal represents a theta wave having a frequency ranging from 0.5 to 7 Hz.

14. A system according to claim 12, wherein the frequency signal represents an alpha wave having a frequency ranging from 7 to 20 Hz.

15. A system according to claim 11, wherein said filter frequency control means comprises means for producing a clock signal having a frequency corresponding to the amplified output, and wherein the passband of said bandpass filter is varied in response to the clock signal.

16. A system according to claim 11, wherein said filter frequency control means comprises means for analyzing the amplified signal by way of fast Fourier transform.

17. A system according to claim 11, wherein said detecting means comprises a pair of electrodes attachable to scalp of the user.

18. A system according to claim 11, wherein said stimulating means comprises a light emitting diode and a driver for energizing said light emitting diode.

19. A system according to claim 11, wherein said stimulating means provides a photic stimulus to the user in synchronism with changes in the amplitude of the stimulative signal.

20. A system according to claim 11, wherein said stimulating means applies an aural stimulus to the user.

21. A system according to claim 11, wherein said stimulating means applies a vibratory stimulus to the user.

22. A system according to claim 17, wherein said detecting means and said stimulating means are incorporated in a headband attachable to the user.

23. A system according to claim 1 wherein said filtering means comprises a bandpass filter; and further comprising,
level adjusting means for adjusting the amplitude of said frequency signal to a predetermined level and outputting a level-adjusted frequency signal to said stimulating means.

24. A system according to claim 23, further comprising:
means for detecting a level of the evoked electroencephalogram signal from the amplitude of the frequency signal extracted by said bandpass filter and aurally informing a condition in which the electroencephalogram signal is evoked.

25. A system according to claim 23, further comprising an amplifier connected to said detecting means for amplifying the signal indicative of the detected physiological change and producing in an output thereof an amplified signal, and wherein said bandpass filter is connected to the output of said amplifier for extracting the frequency signal corresponding to the electroencephalogram signal produced by said amplifier, the frequency signal being converted to the stimulative signal having a variant amplitude.

26. A system according to claim 25, wherein the frequency signal represents a theta wave having a frequency ranging from 0.5 to 7 Hz.

27. A system according to claim 25, wherein the frequency signal represents an alpha wave having a frequency ranging from 7 to 20 Hz.

28. A system according to claim 23, wherein said level adjusting means comprises an automatic gain control circuit.

29. A system according to claim 23, wherein said level adjusting means comprises a limiter.

30. A system according to claim 23, wherein said level adjusting means comprises a clipper.

31. A system according to claim 23, wherein said detecting means comprises a pair of electrodes attachable to a scalp of the user.

32. A system according to claim 23, wherein said stimulating means comprises a light emitting diode and a driver for energizing said light emitting diode.

33. A system according to claim 23, wherein said stimulating means provides a photic stimulus to the user in synchronism with changes in the amplitude of the stimulative signal.

34. A system according to claim 23, wherein said stimulating means applies an aural stimulus to the user.

35. A system according to claim 23, wherein said stimulating means applies a vibratory stimulus to the user.

36. A system according to claim 31, wherein said detecting means and said stimulating means are incorporated in a headband attachable to the user.

37. A system according to claim 1 further comprising:
phase lock signal generator means for generating a signal having a constant level in phase with the signal produced by said detecting means; and wherein said filter means comprises:
first bandpass filter for extracting a frequency signal corresponding to the electroencephalogram signal to be evoked from the signal produced by said phase lock signal generator means.

38. A system according to claim 37, further comprising:
second bandpass filter for removing noise from the signal produced by said detecting means prior to application of said signal to said phase lock signal generator means.

39. A system according to claim 37, further comprising an amplifier connected to said detecting means for amplifying the signal indicative of the detected physiological change and producing in an output thereof an amplified signal, and wherein said second bandpass filter is connected to the output of said amplifier.

40. A system according to claim 39, wherein the frequency signal represents a theta wave having a frequency ranging from 0.5 to 7 Hz.

41. A system according to claim 39, wherein the frequency signal represents an alpha wave having a frequency signal ranging from 7 to 20 Hz.

42. A system according to claim 37, wherein said detecting means comprises a pair of electrodes attachable to a scalp of the user.

43. A system according to claim 37, wherein said stimulating means comprises a light emitting diode and a driver for energizing said light emitting diode.

44. A system according to claim 37, wherein said stimulating means provides a photic stimulus to the user in synchronism with changes in the amplitude of the stimulative signal.

45. A system according to claim 37, wherein said stimulating means applies an aural stimulus to the user.

46. A system according to claim 37, wherein said stimulating means applies a vibratory stimulus to the user.

47. A system according to claim 42, wherein said detecting means and said stimulating means are incorporated in a headband attachable to the user.

48. A system according to claim 1 wherein said filtering means comprises:
a first bandpass filter for extracting a frequency signal corresponding to the electroencephalogram signal to be evoked from the signal produced by said detecting means; and wherein said system further comprises:
pulse width modulator means for generating a signal of a constant level which has been pulse-width modulated by the frequency signal from said bandpass filter;
second bandpass filter for extracting a frequency signal corresponding to an electroencephalogram signal to be evoked from the signal produced by said pulse width modulator means and applying said frequency signal to said stimulating means.

49. A system according to claim 48, further comprising an amplifier connected to said detecting means for amplifying the signal indicative of the detected physiological change and producing in an output thereof an amplified signal, and wherein said first bandpass filter is connected to the output of said amplifier for extracting the frequency signal corresponding to the electroencephalogram signal produced by said amplifier.

50. A system according to claim 49, wherein the frequency signal represents a theta wave having a frequency ranging from 0.5 to 7 Hz.

51. A system according to claim 49, wherein the frequency signal represents an alpha wave having a frequency ranging from 7 to 20 Hz.

52. A system according to claim 48, wherein said detecting means comprises a pair of electrodes attachable to a scalp of the user.

53. A system according to claim 48, wherein said stimulating means comprises a light emitting diode and a driver for energizing said light emitting diode.

54. A system according to claim 48, wherein said stimulating means provides a photic stimulus to the user in synchronism with changes in the amplitude of the stimulative signal.

55. A system according to claim 48, wherein said stimulating means applies an aural stimulus to the user.

56. A system according to claim 48, wherein said stimulating means applies a vibratory stimulus to the user.

57. A system according to claim 52, wherein said detecting means and said stimulating means are incorporated in a headband attachable to the user.

58. A system as claimed in claim 23 further comprising, second detecting means, filtering means, and stimulating means, all being substantially identical to and interconnected substantially identical to the first mentioned detecting means, filtering means, and stimulating means; said first and second detecting means being connected in such a manner to detect brain waves emanating from the right and left cerebral hemispheres, respectively, of the user's body; and said first and second stimulating means being positioned to provide stimulating signals to the left and right cerebral hemispheres, respectively, of the user's body.

59. A system according to claim 1, wherein said stimulating means applies the stimulative signal to the user at a frequency equal to the frequency of said extracted frequency signal.

60. A system for passively evoking desired electroencephalogram signals from right and left cerebral hemispheres, respectively, of a brain of a user, the system, comprising:

detecting means for detecting physiological changes relative to the right and left cerebral hemispheres of the user;

a plurality of bandpass filters for extracting first and second frequency signals from the signals detected by said detecting means, said first and second extracted frequency signals corresponding to detecting physiological changes relative to the right and left cerebral hemisphere of the user's body, respectively;

level adjusting means for adjusting amplitude levels of the extracted first and second frequency signals to respective predetermined levels; and stimulating means, coupled to said level adjusting means, for applying, to the left cerebral hemisphere of the user, a first photic stimulative signal in synchronism with the adjusted first extracted frequency signal, and for applying, to the right hemisphere of the user, a second photic stimulative signal in synchronism with the adjusted second extracted frequency, thereby passively evoking the desired electroencephalogram signals from the user.

* * * * *